United States Patent
Munson et al.

(10) Patent No.: US 6,623,659 B2
(45) Date of Patent: Sep. 23, 2003

(54) SEPARATION OF OLEFINS FROM PARAFFINS USING IONIC LIQUID SOLUTIONS

(75) Inventors: Curtis L. Munson, Oakland, CA (US); Laura C. Boudreau, Lafayette, CA (US); Michael S. Driver, San Francisco, CA (US); William L. Schinski, San Rafael, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 91 days.

(21) Appl. No.: 09/998,138

(22) Filed: Dec. 3, 2001

(65) Prior Publication Data

US 2002/0063240 A1 May 30, 2002

Related U.S. Application Data

(60) Division of application No. 09/735,176, filed on Dec. 12, 2000, which is a continuation-in-part of application No. 09/596,986, filed on Jun. 20, 2000, now abandoned.

(51) Int. Cl.⁷ .................................................. C09K 3/00
(52) U.S. Cl. ...................... 252/184; 585/856; 585/857
(58) Field of Search ......................................... 252/184

(56) References Cited

U.S. PATENT DOCUMENTS

| | | |
|---|---|---|
| 3,304,341 A | 2/1967 | Wiener et al. |
| 3,407,789 A | 10/1968 | Hallee et al. |
| 3,647,682 A | 3/1972 | Rabo et al. |
| 3,679,762 A | 7/1972 | La Hue et al. |
| 3,758,403 A | 9/1973 | Rosinski et al. |
| 3,820,955 A | 6/1974 | Woebcke |
| 4,128,595 A | 12/1978 | Montgomery |
| 4,347,392 A | 8/1982 | Cosyns et al. |
| 4,499,055 A | 2/1985 | DiNicolantonio et al. |
| 4,571,442 A | 2/1986 | Cosyns et al. |
| 4,762,956 A | 8/1988 | Liu et al. |
| 4,814,067 A | 3/1989 | Gartside et al. |
| 4,828,679 A | 5/1989 | Cormier, Jr. et al. |
| 4,980,053 A | 12/1990 | Li et al. |
| 5,059,732 A | 10/1991 | Cosyns et al. |
| 5,326,465 A | 7/1994 | Yongqing et al. |
| 5,712,171 A | 1/1998 | Zambias et al. |
| 5,859,304 A | 1/1999 | Barchas et al. |
| 6,339,182 B1 * | 1/2002 | Munson et al. ............. 585/809 |
| 6,395,948 B1 * | 5/2002 | Hope et al. ................ 585/510 |

FOREIGN PATENT DOCUMENTS

GB        1001886       8/1965

OTHER PUBLICATIONS

Malz Kr., Richard. *Chemical Ind.*, "Catalysis of Organic Reactions," 68:249–263. (1996) Marcel Dekker, Inc., New York.

Enderby, J., *J. Phys. Condens. Matter*, "Ionic Liquids: recent progress and remaining problems", 5:(supp 34B) B99–B106 (1993) Institute of Physics Publishing, UK.

Freemantle, M., *Chemical and Engineering News*, "Designer Solvents", 32–37 (Mar. 30, 1998) American Chemical Society, Washington, D.C.

Gordon, C., et al., *J. Mater. Chem.*, "Ionic liquid crystals: hexafluorophosphate salts", 8: 2627–2636 (1998) The Royal Society of Chemistry, Cambridge, UK.

Seddon, K., *J. Chem. Tech. Biotechnol.*, "Ionic Liquids for Clean Technology", 68: 351–356 (1997) John Wiley & Sons Ltd., UK.

Welton, T., *Chem. Rev.*, "Room–Temperature Ionic Liquids. Solvents for Synthesis and Catalysis", 99: 2071–2084 (1999) American Chemical Society, Washington, D.C.

* cited by examiner

*Primary Examiner*—Margaret Medley
(74) *Attorney, Agent, or Firm*—Burns, Doane, Swecker & Mathis, L.L.P.

(57) ABSTRACT

Methods for separating olefins from non-olefins, such as paraffins, including cycloparaffins, oxygenates and aromatics, are provided. The methods use metal salts to complex olefins, allowing the non-olefins to be separated by a variety of methods, including decantation and distillation. The metal salts are dissolved in ionic liquids, which tend to have virtually no vapor pressure, and which poorly solubilize the non-olefins. Accordingly, the non-olefins phase separate well, and can be distilled without carrying over any of the ionic liquid into the distillate. Preferred salts are Group IB salts, more preferably silver salts. A preferred silver salt is silver tetrafluoroborate. Preferred ionic liquids are those which form stable solutions or dispersions of the metal salts, and which do not dissolve the non-olefins. Further, if the olefins are subject to isomerization, the ionic liquid is preferably relatively non-acidic. The methods involve forming a solution of a suitable olefin-complexing salt in an appropriate ionic liquid. An olefin-containing mixture is contacted with the ionic liquid/salt solution, and the olefins are adsorbed. After the paraffins are removed, the olefins can be isolated by desorption. The olefin-containing mixture can be in the gas phase, or in the liquid phase. The flow of olefin-containing mixtures over/through the ionic liquid can be, for example, co-current, counter-current, or staged in stirred tanks. Countercurrent is preferred as it is the most efficient. The methods can be optimized using combinatorial chemistry.

20 Claims, No Drawings

SEPARATION OF OLEFINS FROM PARAFFINS USING IONIC LIQUID SOLUTIONS

RELATED APPLICATION

This application is a divisional of U.S. patent application Ser. No. 09/735,176, entitled "Separation of Olefins From Paraffins Using Ionic Liquid Solutions" filed on Dec. 12, 2000 which is a continuation in part of application Ser. No. 09/596,986 filed Jun. 20, 2000, now abandoned.

FIELD OF THE INVENTION

The present invention is in the field of organic separations, in particular, separation of olefins from non-olefins such as paraffins, oxygenates and aromatics.

BACKGROUND OF THE INVENTION

There are many product streams, particularly in the field of petroleum chemistry, which include olefins and non-olefins. For example, ethane crackers tend to produce a mixture of ethane and ethylene. The ethylene is typically separated from the ethane via distillation. The boiling points of ethylene and ethane are relatively close to one another, and the distillation is typically done at very low temperatures and/or high pressures. This makes the separation relatively expensive. The same problems are observed when separating propane from propylene in dehydrogenation facilities.

Fischer-Tropsch chemistry tends to provide a variety of gaseous and liquid products, including unreacted synthesis gas, methane, and $C_{2-4}$ hydrocarbons (a mixture of olefins and paraffins). These gases are typically separated from the liquid products. The methane and other light paraffins can be recycled through an upstream synthesis gas generator. However, the light olefins tend to coke the catalysts, and need to be removed before the recycle gas is sent to the synthesis gas generator. The olefins are typically removed via cryogenic separation.

Typically, about 75% of the $C_{2-8}$ products from Fischer-Tropsch synthesis are normal alpha-olefins (NAOs). Separation may be accomplished using conventional distillation. However, there is only a small difference in relative volatility between an olefin and the corresponding paraffin with the same number of carbons. Therefore, distillation requires a large number of stages and/or high reflux ratios. While the olefins are extremely commercially valuable, the commercially available method for separating them is expensive.

Silver and copper salts have been dissolved in aqueous solutions and used to complex olefins. This technology has been proposed for use in separating olefins from paraffins (See, for example, U.S. Pat. No. 5,859,304 to Barchas et al., the contents of which are hereby incorporated by reference). However, there are a number of disadvantages to this approach. Since water has a significant vapor pressure, some water will go into the olefinic product during the regeneration step. The water must therefore be removed from the olefins product. This effect is exasperated since thermal regeneration is one of the preferred methods of regeneration. The high vapor pressure of water also limits the maximum regeneration temperature that can be used. Sweep gases are also sometimes used in the regeneration process, and these will further increase the evaporation of water. Also, water lost in the regeneration step must be replaced and the proper balance of water to complexing agent must be maintained.

It would be advantageous to provide new methods for separating olefins from paraffins. The present invention provides such methods.

SUMMARY OF THE INVENTION

Methods for separating olefins from non-olefins, such as paraffins, including cycloparaffins, oxygenates and aromatics, are provided. The methods use metal salts to complex the olefins, allowing the paraffins to be separated by a variety of methods, including decantation and distillation, preferably extractive distillation. The metal salts are incorporated, e.g., dissolved, in ionic liquids, which tend to have virtually no vapor pressure, and which poorly solubilize paraffins and other non-olefins. Accordingly, the non-olefins phase separate well, and can be decanted or distilled without carrying over any of the ionic liquid.

The olefins can be recovered from the ionic liquids by a number of regeneration options, including any combination of thermal regeneration (increasing the solution temperature to reverse the complexation) and pressure swing regeneration (reducing the pressure to reverse the complexation). Sweep gases may also be used in the regeneration step. Preferred olefin-complexing metal salts are Group IB salts, more preferably silver salts. References to the Periodic Table follow the 1975 rules of the International Union of Pure and Applied Chemistry. A preferred silver salt is silver tetrafluoroborate. Preferred ionic liquids are those which form stable solutions or dispersions of the metal salts, and which do not dissolve unwanted non-olefins. Further, if the olefins are subject to isomerization, and this is undesired, the ionic liquid is preferably relatively non-acidic.

The methods involve forming a solution or dispersion of a suitable olefin-complexing salt in an appropriate ionic liquid. An olefin-containing mixture is contacted with the ionic liquid/salt solution or dispersion, and the olefins are adsorbed. After the non-olefins are removed, the olefins can be isolated by desorption. The olefin-containing mixture can be in the gas phase or in the liquid phase. The flow of olefin-containing mixtures over/through the ionic liquid can be for example, co-current, counter-current, or staged in stirred tanks. Countercurrent is preferred as it is the most efficient.

Silver complexes can be poisoned by various compounds, including sulfur compounds, cyanides and acetylenes. Silver acetylides also pose potential risk of explosion. Accordingly, these compounds should be removed before the mixtures are brought into contact with the ionic liquids. Methods for removing such contaminants are well known to those of skill in the art. One method for removing acetylenes involves complexing the acetylenes with a nickel salt. The resulting nickel acetylides are not explosive. While nickel also complexes olefins, it does so to a significantly lesser degree. Accordingly, a nickel salt can be added to the ionic liquid to form a solutions, suspension or dispersion, acetylides formed, and the solution regenerated in the same ways described above. Alternatively, selective hydrogenation can be used to convert the acetylenes to olefins.

Nickel has been shown to form reversible complexes with acetylene. Unlike silver, Ni does not form the explosive acetylide compound. Dissolving Ni into ionic liquids produces a contacting solution that can be used to safely remove acetylene from olefin streams. While Ni will also complex olefins, it does so to a smaller degree. The solution can be regenerated in the same ways described above.

The methods described herein can be optimized using combinatorial chemistry.

DETAILED DESCRIPTION OF THE INVENTION

The present invention is directed to compositions and methods for separating olefins from non-olefins. The compositions include solutions or dispersions of metal salts, which form complexes with olefins, in ionic liquids. The methods involve contacting a mixture including olefins and non-olefins with a solution of an olefin-complexing metal salt in an ionic liquid. After the non-olefins are separated, the olefins can be removed/desorbed from the ionic liquid.

Olefins

The olefins are preferably $C_{2-50}$ mono-olefins, more preferably $C_{2-20}$ mono-olefins. They may include other functional groups, such as hydroxy groups, carboxylic acid groups, heteroatoms, and the like, provided that such groups do not react with either the olefin-complexing salt or the ionic liquid.

These mono-olefinic compounds can be used commercially to form a wide variety of petrochemicals. For example, these compounds can be used to form polyethylene, polypropylenes, polyisobutylene and other polymers, alcohols, vinyl chloride monomer, acrylonitrile, methyl tertiary butyl ether and other petrochemicals, and a variety of rubbers such as butyl rubber.

Sources of Olefins

The olefins can be derived from a variety of sources. A major source is Fischer-Tropsch synthesis. In Fischer-Tropsch synthesis, the product includes olefins, paraffins and oxygenates. The oxygenates are mostly alcohols, which can be converted to olefins via dehydration over a suitable catalyst. Other commercial sources include wax thermal cracking, the Paragon™ process, ethylene and propylene derived from ethane, ethane/propane (EP cracker) and flexi-crackers (ethylene naphtha cracker), FCC crackers, naphtha crackers, olefins derived from paraffin dehydrogenation, and oligomerization of ethylene and other olefins, methanol-to-olefin processes (methanol cracker) and the like.

Processes for converting hydrocarbons at high temperature, including steam-cracking, catalytic cracking or deep catalytic cracking to produce relatively high yields of unsaturated hydrocarbons, for example, ethylene, propylene, and butenes, are well known in the art. See, for example, U.S. Pat. No. 3,407,789 to Hallee et al., U.S. Pat. No. 3,820,955 to Woebcke, U.S. Pat. No. 4,499,055 to DiNicolantonio, U.S. Pat. No. 4,814,067 to Gartside et al., U.S. Pat. No. 4,828,679 to Cormier, Jr. et al., U.S. Pat. No. 3,647,682 to Rabo et al., U.S. Pat. No. 3,758,403 to Rosinski et al., U.S. Pat. No. 4,814,067 to Gartside et al., U.S. Pat. No. 4,980,053 to Li et al. and U.S. Pat. No. 5,326,465 to Yongqing et al., the contents of which are hereby incorporated by reference.

Non-Olefins

Non-olefins typically include paraffins, oxygenates, and/or aromatics. Additional non-olefins include hydrogen, water, carbon monoxide, carbon dioxide, acetylenes, dienes, and sulfur and nitrogen-containing impurities.

Non-olefins such as paraffins and aromatics are often desirable products. However, if the desired products are olefins, non-olefins may be undesirable products. For example, if NAOs are the desired product of a Fischer-Tropsch synthesis, the oxygenates and paraffins become undesirable products, although they can be preferred for other uses, for example, distillate fuels.

Sulfur and nitrogen impurities are preferably removed. This can be accomplished by hydrotreatment or other means well known to those of skill in the art. For example, extractive Merox is often used to remove sulfur-containing impurities. In one embodiment, the sulfur and nitrogen impurities may be insoluble in the ionic liquid and, if so, are separated from the olefins when the olefins are complexed. Sulfur can be removed with a ZnO guard bed and nitrogen by hydrotreatment and/or acidic super adsorption for basic Nitrogen.

Acetylene impurities are particularly undesirable. They can form salts with various metals and these salts may be explosive. Acetylene impurities are commonly removed by selective hydrogenation. The hydrogenation system may employ any of the catalysts well known to selectively hydrogenate acetylenics and dienes, for example, acetylene, methyl acetylene and propadiene. Group VIII metal hydrogenation catalysts are the most commonly used and are preferred. Group VIII metal hydrogenation catalysts are ordinarily associated with a support, such as alumina. One preferred catalyst is a low surface area granular alumina impregnated with about 0.1 weight percent palladium. Examples of other catalysts which can be used include Raney nickel, ruthenium-on-aluminum, nickel arsenide-on-aluminum, and mixtures thereof. The catalysts ordinarily contain a Group VIII metal in an amount ranging from about 0.01 to about 1 percent by weight of the total catalyst. These and other catalysts are well known to those of skill in the art, and are described, for example, in U.S. Pat. No. 3,679,762 to La Hue et al., U.S. Pat. No. 4,571,442 to Cosyns et al., U.S. Pat. No. 4,347,392 to Cosyns et al. U.S. Pat. No. 4,128,595 to Montgomery, U.S. Pat. No. 5,059,732 to Cosyns et al., and U.S. Pat. No. 4,762,956 to Liu et al., the contents of which are hereby incorporated by reference. Also, nickel salts can be used to selectively complex the acetylenes.

Metal Salts

The metal salts are selected from heavy metal ions which are known to form chemical complexes with olefins, e.g., copper(I), silver(I), gold(I), nickel(II), platinum(II) and palladium(II). Silver (I) salts are particularly preferred. Useful silver(I) salts include silver acetate, silver nitrate, silver fluoride, silver tetrafluoroborate, and mixtures thereof. Silver tetrafluoroborate is particularly preferred. Copper salts include copper halide salts, preferably copper (I) chloride.

The concentration of metal salt in the ionic liquid is typically between about 5 and 20 mole percent salt in the ionic liquid, but the amount can be higher, depending on a variety of factors, including the solubility of the salt in the ionic liquid.

Ionic Liquids

Ionic liquids are organic compounds that are liquid at room temperature. They differ from most salts, in that they have very low melting points. They tend to be liquid over a wide temperature range, are not soluble in non-polar hydrocarbons, are immiscible with water, depending on the anion, and are highly ionizing (but have a low dielectric strength). Ionic liquids have essentially no vapor pressure. Most are air and water stable, and they are used herein to solubilize olefin-complexing metal salts. The properties of the ionic liquids can be tailored by varying the cation and anion. Examples of ionic liquids are described, for example, in *J. Chem. Tech. Biotechnol.*, 68:351–356 (1997); *Chem. Ind.*, 68:249–263 (1996); and *J. Phys. Condensed Matter,* 5:(supp 34B):B99–B106 (1993), *Chemical and Engineering News,* Mar. 30, 1998, 32–37; *J. Mater. Chem.*, 8:2627–2636 (1998); and *Chem. Rev.,* 99:2071–2084 (1999), the contents of which are hereby incorporated by reference.

Many ionic liquids are formed by reacting a nitrogen-containing heterocyclic ring, preferably a heteroaromatic ring, with an alkylating agent (for example, an alkyl halide)

to form a quaternary ammonium salt, and performing ion exchange or other suitable reactions with various Lewis acids or their conjugate bases to form ionic liquids. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this tend to produce low melting solids rather than ionic liquids.

Various triarylphosphines, thioethers and cyclic and non-cyclic quaternary ammonium salts have also been used. Counterions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Certain low melting solids can also be used in place of ionic liquids, depending on the particular separation to be effected. Low melting solids are generally similar to ionic liquids but have melting points between room temperature and about 212° F. or are liquid under the process conditions.

The ionic liquids can either be neutral, acidic or basic. Neutral ionic liquids should be used if the desired olefins are not to be isomerized. If it does not matter whether the olefins are isomerized (and if the olefins and/or non-olefins are not acid-sensitive), either neutral or acidic ionic liquids can be used. Examples of appropriate uses of acidic ionic liquids include where the desired goal is to remove olefins and provide a paraffinic hydrocarbon stream, or where the olefins are already isomerized.

In one embodiment, a library, i.e., a combinatorial library, of ionic liquids is prepared, for example, by preparing various alkyl derivatives of the quaternary ammonium cation, and varying the associated anions. The acidity of the ionic liquids can be adjusted by varying the molar equivalents and type and combinations of Lewis acids.

Methods for Separating Olefins from Non-olefins

Olefins can be selectively removed from mixtures including olefins and non-olefins, such as paraffins and aromatics. The removal involves complexing the olefins with olefin-complexing metals salts which are dissolved or suspended in an ionic liquid, and removing the non-olefins. The non-olefins can be removed, for example, using decantation, distillation and the like, preferably using extractive distillation.

The olefins can then be recovered from the ionic liquids using a number of regeneration options, including any combination of thermal regeneration (increasing the solution temperature to reverse the complexation) and pressure swing regeneration (reducing the pressure to reverse the complexation). Sweep gases may also be used in the regeneration step.

The methods involve forming a solution of a suitable olefin-complexing salt in an appropriate ionic liquid. An olefin-containing mixture is contacted with the ionic liquid/salt solution, and the olefins are adsorbed. After the non-olefins are removed, the olefins can be isolated by desorption. The olefin-containing mixture can be in the gas phase or the liquid phase. The flow of olefin-containing mixtures over/through the ionic liquid can be, for example, co-current, counter-current, or staged in stirred tanks. Countercurrent is preferred as it is the most efficient.

Methods for Desorbing Olefins from the Metal Salt-Complexes

After the olefins have been adsorbed by metal salt/ionic liquid solution or dispersion, and the non-olefins removed, the olefins can be desorbed. Desorption is effected, preferably in a packed tower or flash drum, by dissociating the olefins from the metal salt complexes using a combination of increased temperature and/or lower pressure. At temperatures ranging from about 65° C. to about 110° C., (although higher temperatures may be required for relatively high molecular weight olefins) preferably from about 70° C. to about 85° C., and pressures ranging from about 5 psig to about 50 psig, the olefins readily dissociate from the metal salt complexes. The temperature values would be expected to be higher for higher molecular weight olefins, but should not exceed the decomposition temperature of the ionic liquids. Inexpensive quench water can conveniently be used as the heating medium for olefin stripper temperatures in the lower end of the range, as well as any other heating means known to those of ordinary skill in the art. The olefin stripper is preferably equipped with a water wash section in the top of the stripper to prevent entrainment of the scrubbing solution with the desorbed gases.

The olefin stripper or flash drum may include multi-stage stripping or flashing for increased energy efficiency. In such systems, the olefin-rich solution is flashed and stripped at progressively higher temperatures and/or lower pressures. The design of such systems is well known to those skilled in the art.

The stripped ionic liquid solution can then be removed from the olefin stripper for reclaiming and recycling. Reclaimers typically operate at a higher temperature than olefin strippers. Typically, the temperature in the reclaimer ranges from about 100° C. to about 150° C., preferably from about 120° C. to about 140° C. The pressure ranges from about 5 psig to about 50 psig, preferably from about 10 psig to about 30 psig. The heating duty may be supplied by steam or any other means known to those skilled in the art. At these higher temperatures, residual acetylenes and diolefins, if present, are dissociated from the metal salt complexes.

Commercial Applications

There are many commercial applications for the separation technology described herein. For example, the technology can be used to separate ethylene from ethane in an ethane cracker, ethane/propane cracker or flexi-cracker. Commercially, this has been done using expensive distillation facilities. The present method can be performed at room temperature and atmospheric pressure, resulting in lower processing costs. The major cost is due to the silver ions, which are recycled and reused. Another commercial use is in the separation of propylene from propane, for example, in dehydrogenation facilities. The same situation exists as with ethylene and ethane.

Yet another commercial use is in the separation of light olefins in a Fischer Tropsch recycle tail gas. In Fischer Tropsch synthesis, not all the synthesis gas is converted in each pass through the unit. Methane gas, as well as low molecular weight ($C_{2-4}$, preferably $C_2$ paraffins) are typically recycled in an upstream syngas generator. A problem with the use of this recycle gas is that it often contains olefins. The olefins tend to coke the surfaces of the syngas generators. The olefins in the tail gas contribute most to the coking in comparison to the saturates.

The conventional method for removing the olefins (and other $C_2^+$ components) involves cryogenic separation. The present method involves complexing the olefins with the metal ions in the ionic liquid. A preferred way to do this involves bubbling the olefin-containing stream, preferably in the form of a gas rather than a liquid, through the ionic liquid. Another commercial use of the separation technology involves separating $C_2^+$normal alpha olefins (NAOs) from saturated products derived from Fischer Tropsch Synthesis. NAOs are valuable chemicals and separation technology described herein can readily separate the olefins from the saturates to provide purified NAOs. Similarly, for use in distillate fuel compositions, it is desirable to keep olefin content to a minimum. The technology not only provides NAOs which have a relatively high commercial value, but also provides hydrocarbon compositions which are highly paraffinic and which may have commercial value as distillate fuel compositions without the need of an additional olefin-hydrogenation step.

Combinatorial Chemistry Approaches

A combinatorial approach can be used to identify optimum ionic liquids and/or metal salts for separating the olefins from the non-olefins. An advantage to the combinatorial approach is that the choice of ionic liquid, metal salt and the like can be tailored to specific applications.

The scale of the separations in combinatorial chemistry is preferably in the range of about 1 mg to 200 g, more preferably between 100 mg and 10 g, although the scale can be modified as desired depending on the equipment used. Those of skill in the art can readily determine appropriate sets of reactions and reaction conditions to generate and/or evaluate the libraries of interest.

The ionic liquids can be laid out in a logical fashion in multi-tube arrays or multi-well plates, in the form of arrays of ionic liquids. Preferably, the ionic liquids all have a central core structure, and have various modifications which permit the identification of structure-activity relationships with which to determine optimum compounds for a particular use. The metal salts or combinations thereof can also be laid out in a logical fashion, for example in arrays. In a preferred embodiment, an A×B array is prepared, with various combinations of ionic liquids and metal salts. However, it is also possible to evaluate a single ionic liquid with a plurality of metal salts, and then repeat the process as desired with a plurality of different ionic liquids.

The ability of the particular combination of ionic liquid and metal salt at performing a desired separation can be measured and correlated to specific combinations. The array can be ordered in such a fashion as to expedite synthesis and/or evaluation, to maximize the informational content obtained from the testing and to facilitate the rapid evaluation of that data. Methods for organizing libraries of compounds are well known to those of skill in the art, and are described, for example, in U.S. Pat. No. 5,712,171 to Zambias et al., the contents of which are hereby incorporated by reference.

By screening multiple synthetic variations of a core molecule, the selection of the optimal candidate is more a function of the data collection method than the "rational" basis for selecting a useful ionic liquid. The desired physical and chemical properties for the ionic liquid, when used as a solvent or dispersing agent for a particular metal salt, and for separating a particular product mixture, can be rapidly optimized, and directly correlated with the structural changes within a particular array or sub-array.

The ionic liquids are typically formed by first forming a desired quaternary ammonium salt, and then combining the salt with an appropriate anion precursor (typically a metal salt such as aluminum chloride, zinc chloride, sodium hexafluorophosphate, sodium tetrafluoroborate, hexafluorophosphoric acid, tetrafluoroboric acid and the like). Side product salts can be removed for example by filtration. In cases where the anion precursor was an acid, the acid side product such as HCl can be removed by extraction or by gently heating the ionic liquid under vacuum.

The separations using the ionic liquids/metal salts in the libraries generally involve contacting the appropriate olefin/non-olefin mixtures to ionic liquid/metal salt combinations in the tubes or wells in the multi-tube rack or multi-well plate, and allowing the olefin-complexation reactions to take place, preferably with gentle agitation.

Robotic arms and multi-pipet devices are commonly used to add appropriate reagents to the appropriate tubes in multi-tube racks, or wells in multi-well plates. When appropriate, the chemistry can be performed in an inert atmosphere. The tubes can each be covered with a rubber septum to avoid contamination, and the reagents added via injection.

In one embodiment, the separations are carried out via computer control. The identity of each of the ionic liquids and metal salts can be stored in a computer in a "memory map" or other means for correlating the data regarding the chemical reactions to the ionic liquids in the multi-tube racks or multi-well plates. Alternatively, the separations can be performed manually, preferably in multi-tube racks or multi-well plates, and the information stored, for example, on a computer.

Any type of multi-well plate or multi-tube array commonly used in combinatorial chemistry can be used. Preferably, the number of wells or tubes is in excess of 30, and there is a tube in at least 60 percent of the positions in each multi-tube array. The shape of the rack is not important, but preferably, the rack is square or rectangular. The tubes can be made, for example, from plastic, polymers, glass or metal, such as stainless steel, depending on the type of anions used in the ionic liquid or in the metal salt.

Any type of liquid handler that can add reagents to, or remove reagents from, the wells and/or tubes can be used. Suitable liquid handlers are prepared, for example, by Tecan. Many involve the use of robotic arms and robotic devices. Suitable devices are well known to those of skill in the art of combinatorial chemistry, and include those by Zymart, Gilson, Hamilton, Bodhan and Tecan.

Any device that can take samples from the individual wells and/or tubes and analyze the resulting hydrocarbon phase can be used. Preferably, the device is a chromatographic device, such as an analytical or preparative scale HPLC, GC or column chromatography, although other devices can be envisioned, depending on the chemistry performed. Since the ionic liquid is non-volatile, the sample is preferably taken from the hydrocarbon phase, which is immiscible with the ionic liquid.

Preferably, in those embodiments in which a chromatographic column (HPLC, GC or column chromatography) is used, the device has the ability to identify when the compound of interest is eluting from the column. Various means have commonly been used to identify when compounds of interest are eluting from a column, including UV, IR, TLC, GC-MS, FID, NMR, ELSD, nitrogen detection and the like. Any of these means, and others known to those of skill in the art, can be used, alone or in combination. However, when petroleum chemistry is being evaluated, the product stream often does not include UV-active compounds. In this type of embodiment, the analytical equipment preferably includes an ELSD detector.

The device preferably includes a computer system capable of storing information regarding the identity of the ionic liquids, metal salts and the product streams obtained when combinations of ionic liquids and metal salts are used to separate the olefins from the non-olefins. Software for managing the data is stored on the computer. Relational database software can be used to correlate the identity of the ionic liquids, the metal salts, and the analytical data from each product stream. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the processes described herein. However, any software that is able to create a "memory map" of the ionic liquids in the tubes and correlate that information with the information obtained from the chemical reactions can be used. This type of software is well known to those of skill in the art.

The present invention will be better understood with reference to the following non-limiting examples.

EXAMPLE 1

Synthesis of Neutral Ionic Liquids

A variety of quaternary amine ionic liquid precursors were prepared as follows. 1-Methylimidazole was measured into a stainless-steel autoclave along with a slight molar excess of 1-chlorobutane. The autoclave was sealed, pressurized with 75 psig of nitrogen, and heated to 90° C. for 18 h. The autoclave was then cooled to room temperature and the contents were placed on a rotary evaporator at 95° C. for several hours to remove any unreacted chlorobutane and 1-methylimidazole. A $^1$H NMR of the product indicated the formation of 1-butyl-3-methylimidazolium chloride (bmim$^+$Cl$^-$). The reaction was repeated with 1-chlorohexane to give 1-hexyl-3-methylimidazolium chloride (hmim$^+$Cl$^-$). This general procedure was repeated with pyridine to give the ionic liquid precursors N-butylpyridinium chloride (butpyr$^+$Cl$^-$) and N-hexylpyridinium chloride (hexpyr$^+$Cl$^-$), although a higher reaction temperature (130° C.) was required to achieve high yields.

Two different procedures were used for conducting an anion exchange reaction to give a neutral ionic liquid. In one procedure, the precursor is dissolved in acetone and reacted with the sodium salt of the desired anion (NaBF$_4$ or NaPF$_6$). In the other procedure, the precursor is dissolved in water and reacted with the acid form of the anion (HBF$_4$ or HPF$_6$). The precursor hmim$^+$Cl$^-$ was used make the ionic liquid hmim$^+$PF$_6^-$ by both procedures. The miscibility of the resulting ionic liquid with water was greatly influenced by the route of synthesis. The ionic liquid made by the acid route was immiscible with water, while the ionic liquid made using the sodium salt was miscible with water. While not wishing to be bound to a particular theory, it is believed that this change in miscibility with water is due to the presence of residual NaCl in the liquid made via the salt route.

The acid procedure was then used to generate a variety of ionic liquids using the precursors synthesized above, as well as additional precursors purchased from commercial suppliers. These reactions are summarized in Table 1. Not all of the combinations resulted in the formation of room temperature ionic liquids. Highly symmetric cations (Me$_4$N$^+$) and cations with long alkyl chains (C$_{16}$NMe$_3^+$) tend to give solid products with high melting points (>100° C.). The reactions that did not result in room temperature ionic liquids are shown in Table 2.

TABLE 1

Neutral Ionic Liquids

| Ionic Liquid precursor | anion source | Ionic Liquid |
|---|---|---|
| bmim$^+$Cl$^-$ | HBF$_4$ | bmim$^+$BF$_4^-$ |
| bmim$^+$Cl$^-$ | HPF$_6$ | bmim$^+$PF$_6^-$ |
| hmim$^+$Cl$^-$ | NaBF$_4$ | hmim$^+$BF$_4^-$ |
| hmim$^+$Cl$^-$ | HBF$_4$ | hmim$^+$BF$_4^-$ |
| hmim$^+$Cl$^-$ | NaPF$_6$ | hmim$^+$PF$_6^-$ |
| hmim$^+$Cl$^-$ | HPF$_6$ | hmim$^+$PF$_6^-$ |
| hexpyr$^+$Cl$^-$ | HBF$_4$ | hexpyr$^+$BF$_4^-$ |
| hexpyr$^+$Cl$^-$ | HPF$_6$ | hexpyr$^+$PF$_6^-$ (mp = 38.7 1 C) |
| (C$_8$H$_{17}$)$_3$MeN$^+$Cl$^-$ | HBF$_4$ | (C$_8$H$_{17}$)$_3$MeN$^+$BF$_4^-$ (mp = 58.8° C.) |
| (C$_8$H$_{17}$)$_3$MeN$^+$Cl$^-$ | HPF$_6$ | (C$_8$H$_{17}$)$_3$MeN$^+$ PF$_6$ |
| Bu$_2$Me$_2$N$^+$Cl$^-$ | HBF$_4$ | Bu$_2$Me$_2$N$^+$BF4$^-$ (mp = 75.1 1C) | bmim = 1-butyl-3-methylimidazolium
hexpyr = N-hexylpyridinium
bmim = 1-hexyl-3-methylimidizolium

TABLE 2

Reactions That Did Not Result in Room Temperature Ionic Liquids

| Ionic Liquid precursor | anion source | solid product |
|---|---|---|
| Me$_3$NH$^+$Cl$^-$ | HBF$_4$ | Me$_3$NH$^+$BF4 – (mp = 183° C.) |
| Me$_3$NH$^+$Cl$^-$ | HPF$_6$ | Me$_3$NH$^+$PF$_6^-$ |
| Me$_4$N$^+$Cl$^-$ | HPF$_6$ | Me$_4$N$^+$PF$_6^-$ |
| Me$_4$N$^+$Cl$^-$ | NaBF$_4$ | Me$_4$N$^+$BF$_4^-$ |
| Bu$_2$Me$_2$N$^+$Cl$^-$ | HPF$_6$ | Bu$_2$Me$_2$N$^+$PF$_6^-$(mp = 154.5° C.) |
| (C$_{16}$H$_{33}$)Me$_3$N$^+$Cl$^-$ | HBF$_4$ | (C$_{16}$H$_{33}$)Me$_3$N$^+$BF$_4^-$ |
| (C$_{16}$H$_{33}$)Me$_3$N$^+$Cl$^-$ | HPF$_6$ | (C$_{16}$H$_{33}$)Me$_3$N$^+$PF$_6^-$(mp = 131.7° C.) |
| hexPPh$_3^+$Br$^-$ | NaPF$_6$ | hexPPh$_3^+$PF$_6^-$ | hexPPh$_3$ = hexyltriphenyiphosphonium

EXAMPLE 2

Solubility of Cu and Ag Complexes in Ionic Liquids

The present example investigated the possibility of immobilizing Ag and Cu ions in an ionic liquid. The Ag(l) and Cu(I) compounds have been proposed for use in the selective complexation of dienes over mono-olefins. The immobilization of these ions can be accomplished by either dissolving Ag and Cu salts in an existing ionic liquid or by reacting an ionic liquid precursor with a Ag or Cu complex to create a new ionic liquid.

Several screening reactions were conducted to determine whether Ag and Cu complexes were soluble in ionic liquids. The results are summarized in Table 3.

TABLE 3

Solubility of Ag and Cu Ion in Ionic Liquids

| Ionic Liquid or Precursor | Salt | Soluble? |
|---|---|---|
| bmim$^+$BF$_4^-$ | AgBF$_4$ | yes |
| bmim$^+$PF$_6^-$ | AgPF$_6$ | no |
| bmim$^+$Cl$^-$ | AgCl | no |
| hmim$^+$Cl$^-$ | AgCl | no |
| hexpyr$^+$Cl$^-$ | AgCl | no |
| bmim$^+$Cl$^-$ | CuCl | yes |
| hmim$^+$Cl$^-$ | CuCl | yes |
| hexpyr$^+$Cl$^-$ | CuCl | yes |

As shown above, an attempt was made to dissolve the Ag salts in ionic liquids that contained the same anions. For example, AgBF$_4$ was combined with bmim$^+$BF4$^-$ and AgPF$_6$ was combined with bmim$^+$PF$_6^-$. AgBF$_4$ was soluble in an ionic liquid. Neither AgPF$_6$ nor AgCl dissolved in the ionic liquids that were tested. Attempts were made to dissolve CuCl in a couple of different ionic liquids and ionic liquid precursors. The CuCl dissolved in bmim$^+$Cl$^-$, hmim$^+$ cl$^-$, and hexpyr$^+$Cl$^-$. It is believed that the CuCl participated in a complexation reaction to give new ionic liquids with CuCl$_2^-$ anions.

EXAMPLE 3

Use of Ionic Liquids Containing Ag(I) and Cu(I) Salts for Olefin Coordination

This example evaluated the use of Ag(I) and Cu(I) compounds immobilized in ionic liquids for the complexation of olefins. The adsorption of i-butene gas by the ionic liquid samples was measured and is summarized in Table 4. The ionic liquid samples containing varying amounts of dissolved AgBF$_4$ showed reversible adsorption of the butene gas while the ionic liquids containing the CuCl$_2^-$ anion did not show any appreciable adsorption.

As a control experiment, the Ag-containing ionic liquids were also tested for butane adsorption. No appreciable adsorption was detected. This again suggests that the Ag is forming a complex with the olefin and that the gases are not merely dissolving in the ionic liquid.

TABLE 4

Gas Adsorption by Ionic Liquids Containing Ag(1) and Cu(I) salts.

| Ionic Liquid | salt | gas | wt % gas absorbed | mols gas/ mols M(I) |
|---|---|---|---|---|
| bmim$^+$BF4$^-$ | 5% AgBF$_4$ | 1-butene | 1.45 | 1.32 |
| bmim$^+$BF4$^-$ | 10% AgBF$_4$ | 1-butene | 1.89 | 0.87 |
| bmim$^+$BF4$^-$ | 25% AgBF$_4$ | 1-butene | 7.69 | 1.30 |
| bmim$^+$Cl$^-$ | 1.0 equiv. CuCl | 1-butene | 0.03 | nc |
| bmim$^+$Cl$^-$ | 2.0 equiv. CuCl | 1-butene | 0.15 | nc |
| hexpyr$^+$Cl$^-$ | 1.0 equiv. CuCl | 1-butene | 0.60 | nc |
| bmim$^+$BF4$^-$ | 5% AgBF$_4$ | butane | 0.13 | 0.10 |
| bmim$^+$BF4$^-$ | 10% AgBF$_4$ | butane | 0 | 0 |
| bmim$^+$BF4$^-$ | 25% AgBF$_4$ | butane | 2.56 | 0.35 | bmim = 1-butyl-3-methylimidazolium;
hexpyr = N-hexylpyridinium;
nc = not calculated While the invention has been described with preferred embodiments, it is to be understood that variations and modifications may be resorted to as will be apparent to those skilled in the art. Such variations and modifications are to be considered within the purview and scope of the claims appended hereto.

What is claimed:

1. A composition useful for purification of olefins comprising an ionic liquid and a metal salt dissolved or dispersed in the ionic liquid.

2. The composition of claim 1 wherein the metal salt is dissolved in the ionic liquid.

3. The composition of claim 2, wherein the metal salt is a Group IB salt.

4. The composition of claim 1, wherein the metal salt is selected from the group consisting of copper (I), silver (I), gold (I), nickel (II), platinum (II), palladium (II), and mixtures thereof.

5. The composition of claim 4, wherein the metal salt is a silver salt.

6. The composition of claim 5, wherein the silver salt is selected from the group consisting of silver acetate, silver nitrate, silver fluoride, silver tetrafluoroborate, and mixtures thereof.

7. The composition of claim 6, wherein the silver salt is silver tetrafluoroborate.

8. The composition of claim 4, wherein the metal salt is a copper halide salt.

9. The composition of claim 1, wherein the ionic liquid is a neutral ionic liquid.

10. The composition of claim 4, wherein the metal salt is a mixture of a silver salt and a copper salt.

11. The composition of claim 1, wherein the ionic liquid comprises a nitrogen-containing heterocyclic ring.

12. The composition of claim 1, wherein the ionic liquid comprises a nitrogen-containing heteroaromatic.

13. The composition of claim 12, wherein the nitrogen-containing heteroaromatic is selected from the group consisting of pyridines, substituted pyridines, imidazole, substituted imidazole, pyrrole, substituted pyrroles, and mixtures thereof.

14. The composition of claim 1, wherein the ionic liquid is selected from the group consisting of 1-butyl-3-methylimidazolium tetrafluoroborate, 1-butyl-3-methylimidizolium hexafluorophosphate, 1-hexyl-3-methylimidizolium tetrafluoroborate, 1-hexyl-3-methylimidizolium hexafluorophosphate, N-hexylpyridinium tertrafluoroborate, N-hexylpyridinium hexafluorophosphate, (C$_8$H$_{17}$)$_3$MeN$^+$BF$_4$, (C$_8$H$_{17}$)$_3$MeN$^-$PF6, and Bu$_2$Me$_2$N$^+$BF4.

15. The composition of claim 1, wherein the metal salt is in the ionic liquid in a concentration of about 5–20 mol %.

16. A solution useful for purification of olefins comprising an olefin-complexing salt and an ionic liquid.

17. The composition of claim 16, wherein the olefin-complexing salt is a silver salt.

18. The composition of claim 17, wherein the silver salt is silver tetrafluoroborate.

19. The composition of claim 17, further comprising a copper (I) salt.

20. A composition useful for purification of olefins comprising an ionic liquid and an olefin-complexing silver salt dissolved in the ionic liquid in a concentration of about 5–20 mol %.

* * * * *

UNITED STATES PATENT AND TRADEMARK OFFICE
CERTIFICATE OF CORRECTION

PATENT NO. : 6,623,659 B2
DATED : September 23, 2003
INVENTOR(S) : Munson et al.

It is certified that error appears in the above-identified patent and that said Letters Patent is hereby corrected as shown below:

<u>Column 12,</u>
Lines 39-40, please delete "$(C_8H_{17})_3MeN^-\ PF6$, and $Bu_2Me_2N\ ^+BF4$.", and insert therefor -- $(C_8H_{17})_3MeN\ ^+PF6$, and $Bu_2Me_2N\ ^+BF4^-$. --

Signed and Sealed this

Thirteenth Day of January, 2004

JON W. DUDAS
*Acting Director of the United States Patent and Trademark Office*